United States Patent
Flohr et al.

(10) Patent No.: US 7,588,777 B2
(45) Date of Patent: *Sep. 15, 2009

(54) SURFACE CROSS-LINKED SUPERABSORBENT POLYMER PARTICLES AND METHODS OF MAKING THEM

(75) Inventors: Andreas Flohr, Kronberg (DE); Torsten Lindner, Kronberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 468 days.

This patent is subject to a terminal disclaimer.

(21) Appl. No.: 11/183,356

(22) Filed: Jul. 18, 2005

(65) Prior Publication Data

US 2006/0020053 A1 Jan. 26, 2006

(30) Foreign Application Priority Data

Jul. 20, 2004 (EP) .................................. 04017071

(51) Int. Cl.
*A61L 15/16* (2006.01)
*A61L 15/60* (2006.01)
*C08F 8/14* (2006.01)
*C08F 8/28* (2006.01)

(52) U.S. Cl. ...................... 424/443; 424/489; 522/88; 522/121; 522/130; 525/329.7

(58) Field of Classification Search ................. 522/121, 522/129, 88; 526/316; 525/329.7; 424/443, 424/489; 428/500

See application file for complete search history.

(56) References Cited

U.S. PATENT DOCUMENTS

| | | | |
|---|---|---|---|
| 3,661,875 A | 5/1972 | Sieja | |
| 3,860,003 A | 1/1975 | Buell | |
| 3,935,099 A | 1/1976 | Weaver et al. | |
| 3,959,569 A | 5/1976 | Burkholder, Jr. et al. | |
| 4,062,817 A | 12/1977 | Westerman | |
| 4,076,663 A | 2/1978 | Masuda et al. | |
| 4,093,776 A | 6/1978 | Aoki et al. | |
| 4,124,748 A | 11/1978 | Fujimoto et al. | |
| 4,286,082 A | 8/1981 | Tsubakimoto | |

(Continued)

FOREIGN PATENT DOCUMENTS

EP 0 246 848 A 11/1987

(Continued)

OTHER PUBLICATIONS

WO 03/104300, BASF Aktiengellschaft, Dec. 18, 2003.*

(Continued)

*Primary Examiner*—Susan W Berman
(74) *Attorney, Agent, or Firm*—Eric T. Addington; John G. Powell

(57) ABSTRACT

The present invention relates to superabsorbent polymer particles with improved surface cross-linking and their use in absorbent articles.

The superabsorbent polymer particles of the present invention comprise polymer chain segments, wherein at least a part of the polymer chain segments are covalently cross-linked to each other and wherein at least a part of the cross-links comprise the reaction product of cross-linking molecules having at least two C=C double bonds and further comprise the reaction product of radical former molecules. These cross-links are present at surfaces of the superabsorbent polymer particles.

Moreover, the invention relates a method for making these superabsorbent polymer particles.

13 Claims, 2 Drawing Sheets

U.S. PATENT DOCUMENTS

| | | | |
|---|---|---|---|
| 4,367,323 A | 1/1983 | Kitamura | |
| 4,389,513 A | 6/1983 | Miyazaki | |
| 4,446,261 A | 5/1984 | Yamasaki et al. | |
| 4,610,678 A | 9/1986 | Weisman et al. | |
| 4,625,001 A | 11/1986 | Tsubakimoto et al. | |
| 4,654,039 A | 3/1987 | Brandt et al. | |
| 4,666,983 A | 5/1987 | Tsubakimoto et al. | |
| 4,683,274 A | 7/1987 | Nakamura et al. | |
| 4,690,996 A | 9/1987 | Shih et al. | |
| 4,721,647 A | 1/1988 | Nakanishi et al. | |
| 4,734,478 A | 3/1988 | Tsubakimoto et al. | |
| 4,738,867 A | 4/1988 | Itoh et al. | |
| 4,748,076 A | 5/1988 | Saotome | |
| 4,769,427 A | 9/1988 | Nowakowsky et al. | |
| 4,783,510 A | 11/1988 | Saotome | |
| 4,834,735 A | 5/1989 | Alemany et al. | |
| 4,873,299 A | 10/1989 | Nowakowsky et al. | |
| 4,910,250 A | 3/1990 | Saotome | |
| 4,940,464 A | 7/1990 | Van Gompel et al. | |
| 4,950,692 A | 8/1990 | Lewis et al. | |
| 4,973,632 A | 11/1990 | Nagasuna et al. | |
| 4,985,518 A | 1/1991 | Alexander et al. | |
| 5,124,416 A | 6/1992 | Haruna et al. | |
| 5,128,386 A | 7/1992 | Rehmer et al. | |
| 5,135,209 A * | 8/1992 | Penny | 269/249 |
| 5,137,537 A | 8/1992 | Herron | |
| 5,145,906 A | 9/1992 | Chambers et al. | |
| 5,147,345 A | 9/1992 | Young et al. | |
| 5,151,092 A | 9/1992 | Buell et al. | |
| 5,223,645 A | 6/1993 | Barwich et al. | |
| 5,244,735 A | 9/1993 | Kimura et al. | |
| 5,248,805 A | 9/1993 | Boettcher et al. | |
| 5,250,640 A | 10/1993 | Irie et al. | |
| 5,260,345 A | 11/1993 | Desmarais et al. | |
| 5,264,495 A | 11/1993 | Irie et al. | |
| 5,264,533 A | 11/1993 | Rehmer et al. | |
| 5,275,773 A | 1/1994 | Irie et al. | |
| 5,342,338 A | 8/1994 | Roe et al. | |
| 5,380,808 A | 1/1995 | Sumiya et al. | |
| 5,387,207 A | 2/1995 | Dyer | |
| 5,389,699 A | 2/1995 | Rehmer et al. | |
| 5,397,316 A | 3/1995 | Lavon | |
| 5,422,405 A | 6/1995 | Dairoku et al. | |
| 5,478,879 A | 12/1995 | Kajikawa et al. | |
| 5,554,145 A | 9/1996 | Roe et al. | |
| 5,569,234 A | 10/1996 | Buell et al. | |
| 5,597,873 A * | 1/1997 | Chambers et al. | 525/330.1 |
| 5,625,222 A | 4/1997 | Yoneda et al. | |
| 6,004,306 A | 12/1999 | Robles et al. | |
| 6,007,833 A * | 12/1999 | Chudzik et al. | 424/425 |
| 6,228,930 B1 | 5/2001 | Dairoku et al. | |
| 6,359,049 B1 | 3/2002 | Carrico et al. | |
| 6,803,107 B2 * | 10/2004 | Mitchell et al. | 428/403 |
| 7,135,209 B2 * | 11/2006 | Daniel et al. | 427/513 |
| 7,166,356 B2 * | 1/2007 | Flohr | 428/403 |
| 7,199,211 B2 * | 4/2007 | Popp et al. | 528/274 |
| 7,259,212 B2 | 8/2007 | Popp et al. | |
| 7,405,321 B2 | 7/2008 | Riegel et al. | |
| 7,420,013 B2 | 9/2008 | Riegel et al. | |
| 2003/0045847 A1 * | 3/2003 | Whitmore et al. | 604/368 |
| 2003/0135172 A1 * | 7/2003 | Whitmore et al. | 604/359 |
| 2003/0233082 A1 | 12/2003 | Kline et al. | |
| 2004/0143030 A1 | 7/2004 | Ikkai | |
| 2004/0167486 A1 | 8/2004 | Busam et al. | |
| 2005/0048221 A1 * | 3/2005 | Irie et al. | 427/558 |
| 2005/0215752 A1 | 9/2005 | Popp et al. | |
| 2005/0234410 A1 | 10/2005 | Ashton et al. | |
| 2006/0020078 A1 | 1/2006 | Popp et al. | |
| 2006/0052478 A1 | 3/2006 | Madsen et al. | |
| 2006/0212011 A1 | 9/2006 | Popp et al. | |
| 2006/0235141 A1 | 10/2006 | Riegel et al. | |
| 2006/0247377 A1 | 11/2006 | Riegel et al. | |
| 2007/0015860 A1 * | 1/2007 | Frank | 524/450 |
| 2007/0082142 A1 * | 4/2007 | Flohr | 427/457 |

FOREIGN PATENT DOCUMENTS

| | | |
|---|---|---|
| EP | 0248437 A2 | 12/1987 |
| EP | 0514775 A1 | 11/1992 |
| EP | 287970 B1 | 1/1994 |
| EP | 811636 B1 | 8/2001 |
| EP | 1178059 A2 | 2/2002 |
| EP | 456136 B1 | 3/2002 |
| EP | 955086 B1 | 9/2003 |
| EP | 844270 B1 | 11/2004 |
| EP | 922717 B1 | 1/2005 |
| EP | 1 506 788 A | 2/2005 |
| EP | 1516884 A2 | 3/2005 |
| EP | 1624002 A | 2/2006 |
| EP | 1757646 A | 2/2007 |
| JP | 01 092226 A | 4/1989 |
| JP | 01 292103 A | 11/1989 |
| JP | 2003 156961 A | 5/2003 |
| WO | WO-93/16131 A1 | 8/1993 |
| WO | WO 02/094328 A | 11/2002 |
| WO | WO 03/043670 A1 | 5/2003 |
| WO | WO 2005/044915 A1 | 5/2005 |
| WO | WO 2005/097313 A1 | 10/2005 |

OTHER PUBLICATIONS

PCT Search Report, mailed Apr. 13, 2006, 5 pages.

Y. Tang, R.P. Thorn, R.L. Mauldin III, P.H. Wine, Kinetics And Spectroscopy Of the $SO_4$-Radical In Aqueous Solution, Journal of Photochemistry and Photobiology, A: Chemistry, 44(1988), pp. 243-258, Elsevier Sequoia/Printed in The Netherlands.

Om P. Chawla and Richard W. Fessenden, Electron Spin Resonance and Pulse Radiolysis Studies Of Some Reactions of $SO_4$, Radiation Research Laboratories and Department of Chemistry, Mellon Institute of Science, Carnegie-Mellon University, Pittsburgh, Pennsylvania 15213, The Journal of Physical Chemistry, vol. 79, No. 24, 1975.

International Search Report dated Jul. 30, 2008 (4 pages).

* cited by examiner

SURFACE CROSS-LINKED SUPERABSORBENT POLYMER PARTICLES AND METHODS OF MAKING THEM

FIELD OF THE INVENTION

The present invention relates to superabsorbent polymer particles with improved surface cross-linking and their use in absorbent articles.

Moreover, the invention relates to a process for making these superabsorbent polymer particles.

BACKGROUND OF THE INVENTION

Superabsorbent polymers (SAPs) are well known in the art. They are commonly applied in absorbent articles, such as diapers, training pants, adult incontinence products and feminine care products to increase the absorbent capacity of such products while reducing their overall bulk. The SAPs generally are capable of absorbent and retaining amounts of aqueous fluids equivalent to many times their own weight.

Commercial production of SAPs began in Japan in 1978. The early superabsorbent was a cross-linked starch-g-polyacrylate. Partially neutralized polyacrylic acid eventually replaced earlier superabsorbents in the commercial production of SAPs, and is the primary polymer employed for SAPs today. SAPs are often applied in form of small particles, such as fibers or granules. They generally consist of a partially neutralized lightly cross-linked polymer network, which is hydrophilic and permits swelling of the network once submerged in water or an aqueous solution such as physiological saline. The cross-links between the polymer chains assure that the SAP does not dissolve in water.

After absorption of an aqueous solution, swollen SAP particles become very soft and deform easily. Upon deformation the void spaces between the SAP particles are blocked, which drastically increases the flow resistance for liquids. This is generally referred to as "gel-blocking". In gel blocking situations liquid can move through the swollen SAP particles only by diffusion, which is much slower than flow in the interstices between the SAP particles.

One commonly applied way to reduce gel blocking is to make the particles stiffer, which enables the SAP particles to retain their original shape thus creating or maintaining void spaces between the particles. A well-known method to increase stiffness is to cross-link the carboxyl groups exposed on the surface of the SAP particles. This method is commonly referred to as surface cross-linking.

The art refers e.g. to surface cross-linked and surfactant coated absorbent resin particles and a method of their preparation. The surface cross-linking agent can be a polyhydroxyl compound comprising at least two hydroxyl groups, which react with the carboxyl groups on the surface of the SAP particles. In some art, surface cross-linking is carried out at temperatures of 150° C. or above. The particles are preferably exposed to the elevated temperatures for at least 5 minutes but less than 60 minutes.

Another known method for surface cross-linking absorbent resins uses the carboxyl groups of the polymer, which are comprised on the surface of the resin, react with a polyhydric alcohol. The reaction can be accomplished at temperatures in the range of 90° C. to 250° C.

It is also know that hydroxyalkylurea or hydroxyalkylamide can be used as cross-linking agent. In both cases the surface cross-linking reaction can be carried out at temperatures from about 90° C. to about 170° C. for 60 to 180 minutes.

A water-soluble peroxide radical initiator as surface cross-linking agent is also known. An aqueous solution containing the surface cross-linking agent is applied on the surface of the polymer. The surface cross-linking reaction is achieved by heating to a temperature such that the peroxide radical initiator is decomposed while the polymer is not decomposed.

More recently the use of an oxetane compound and/or an imidazolidinone compound for use as surface cross-linking agent has been disclosed. The surface cross-linking reaction can be carried out under heat, wherein the temperature is preferably in the range of 60° C. to 250° C. Alternatively, the surface cross-linking reaction can also be achieved by a photo-irradiation treatment, preferably using ultraviolet rays.

In general, the surface cross-linking agent is applied on the surface of the SAP particles. Therefore, the reaction preferably takes place on the surface of the SAP particles, which results in improved cross-linking on the surface of the particles while not substantially affecting the core of the particles. Hence, the SAP particles become stiffer and gel-blocking is reduced.

A drawback of the commercial surface cross-linking process described above is, that it takes relatively long, commonly at least about 30 min. However, the more time is required for the surface cross-linking process, the more surface cross-linking agent will penetrate into the SAP particles, resulting in increased cross-linking inside the particles, which has a negative impact on the capacity of the SAP particles. Therefore, it is desirable to have short process times for surface cross-linking. Furthermore, short process times are also desirable with respect to an overall economic SAP particle manufacturing process.

Another drawback of common surface cross-linking processes is, that they take place only under relatively high temperatures, often around 150° C. or above. At these temperatures, not only the surface cross-linker reacts with the carboxyl groups of the polymer, but also other reactions are activated, e.g. anhydride-formation of neighbored carboxyl groups within or between the polymer chains, and dimer cleavage of acrylic acid dimers incorporated in the SAP particles. Those side reactions also affect the core, decreasing the capacity of the SAP particles. In addition, exposure to elevated temperatures can lead to color degradation of the SAP particles. Therefore, these side reactions are generally undesirable.

SAPs known in the art are typically partially neutralized, e.g. with sodium hydroxide. However, neutralization has to be carefully balanced with the need for surface cross-linking: The surface cross-linking agents known in the art only react with free carboxyl groups comprised by the polymer chains but they are not able to react with a neutralized carboxyl groups. Thus, the carboxyl groups can either be applied for surface cross-linking or for neutralization, but the same carboxyl group cannot be applied to fulfill both tasks. Surface cross-linking agents known in the art do not react with chemical groups other than carboxyl groups, e.g. they do not react with aliphatic groups.

In the process of making SAP particles, neutralization of free carboxyl groups typically comes first, before surface cross-linking takes place. Indeed, the neutralization step is often carried out in the very beginning of the process, before the monomers are polymerized and cross-linked to form the SAP. Such a process is named 'pre-neutralization process'. Alternatively, the SAP can be neutralized in the middle of polymerization or after polymerization ('post-neutralization'). Furthermore, a combination of these alternatives is also possible.

As the overall number of free carboxyl groups on the outer surface of the SAP particles is limited by the foregoing neutralization, it is very difficult to obtain particles with a high degree of surface cross-linking and hence, a high stiffness to reduce gel-blocking. Furthermore, it is very difficult to obtain SAP particles with evenly distributed surface cross-linking, as the remaining free carboxyl groups are not only few in number but generally also randomly distributed, which sometimes results in SAP particles with regions of rather dense surface cross-linking and regions of sparsely surface cross-linking.

It is therefore an objective of the present invention to provide SAP particles, which have a high degree of surface cross-linking and at the same time allow for a high degree of neutralization.

It is a further objective of the present invention to provide SAP particles with evenly distributed, homogenous surface cross-linking.

Furthermore, it is an objective of the present invention to provide a process to produce SAP particles with the above-mentioned advantages.

It is a still further objective of the present invention to provide a process to produce SAP particles, wherein the process step of surface cross-linking can be carried out quickly to increase the efficiency of the process.

Moreover, a further objective of the present invention is to provide a process to produce SAP particles, which can be carried out at moderate temperatures in order to reduce undesired side reactions, such as anhydride-formation and dimer cleavage.

SUMMARY OF THE INVENTION

The present invention relates to superabsorbent polymer particles comprising polymer chain segments,
- wherein at least some of the polymer chain segments are covalently cross-linked to each other after formation of the superabsorbent polymer particles, and
- wherein the cross-links comprise the reaction product of cross-linking molecules having at least two C═C double bonds, and wherein the cross-links further comprise the reaction product of radical former molecules, and
- wherein the cross-links are present on the surface of the superabsorbent polymer particles.

The present invention further relates to a method of surface cross-linking superabsorbent polymer particles which comprises the steps of
a) providing superabsorbent polymer particles comprising polymer chain segments,
b) adding a surface cross-linking composition comprising cross-linking molecules having at least two C═C double bonds and further comprising radical former molecules,
c) exposing the superabsorbent polymer particles and the surface cross-linking composition to electromagnetic irradiation capable of activating the radical former, whereby the cross-linking molecules and the radical former molecules react with at least some of the polymer chain segments comprised at surfaces of the superabsorbent polymer particles to form covalent cross-links between the polymer chain segments, wherein the cross-links comprise the reaction product of the cross-linking molecule and wherein the cross-links further comprise the reaction product of the radical former molecules.

Moreover, the present invention relates to absorbent products comprising the superabsorbent polymer particles of the present invention.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

The SAPs according to the present invention comprise a homopolymer of partially neutralized $\alpha,\beta$-unsaturated carboxylic acid or a copolymer of partially neutralized $\alpha,\beta$-unsaturated carboxylic acid copolymerized with a monomer copolymerizable therewith. Furthermore, the homo-polymer or copolymer comprised by the SAP comprises aliphatic groups, wherein at least some of the aliphatic groups are at least partially exposed on the surface of the superabsorbent polymer particles SAPs are available in a variety of chemical forms, including substituted and unsubstituted natural and synthetic polymers, such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, SAPs useful herein have a multiplicity of anionic, functional groups, such as sulfonic acid, and more typically carboxyl groups. Examples of polymers suitable for use herein include those, which are prepared from polymerizable, unsaturated, acid-containing monomers. Thus, such monomers include the olefinically unsaturated acids and anhydrides that contain at least one carbon-to-carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing SAPs. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 and in U.S. Pat. No. 4,062,817.

Olefinically unsaturated carboxylic acid and carboxylic acid anhydride monomers include the acrylic acids typified by acrylic acid itself, methacrylic acid, ethacrylic acid, $\alpha$-chloroacrylic acid, $\alpha$-cyanoacrylic acid, $\beta$-methylacrylic acid (crotonic acid), $\alpha$-phenylacrylic acid, $\beta$-acryloxypropionic acid, sorbic acid, $\alpha$-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred SAPs according to the present invention contain carboxyl groups. These polymers comprise hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid, partially neutralized polymethacrylic acid, and slightly network crosslinked polymers of partially neutralized polymethacrylic acid. These polymers can be used either solely or in the form of a mixture of two or more different polymers, that when used as mixtures, individually do not have to be partially neutralized, whereas the resulting copolymer has to be. Examples of these polymer materials are disclosed in U.S. Pat. Nos. 3,661,875, 4,076,663, 4,093,776, 4,666,983, and 4,734,478.

Most preferred polymer materials for use herein are slightly network crosslinked polymers of partially neutralized polyacrylic acids, slightly network crosslinked polymers of partially neutralized polymethacrylic acids, their copolymers and starch derivatives thereof. Most preferably, SAPs comprise partially neutralized, slightly network crosslinked, polyacrylic acid (i.e. poly (sodium acrylate/acrylic acid)). Preferably, the SAPs are at least 50%, more preferably at least 70%, even more preferably at least 75% and even more preferably from 75% to 95% neutralized. Network crosslinking renders the polymer substantially water-insoluble and, in part, determines the absorptive capacity of the hydrogel-forming absorbent polymers. Processes for network crosslinking these polymers and typical network crosslinking agents are described in greater detail in U.S. Pat. No. 4,076,663.

A suitable method for polymerizing the α,β-unsaturated carboxylic acid monomers is aqueous solution polymerization, which is well known in the art. An aqueous solution comprising α,β-unsaturated carboxylic acid monomers and polymerization initiator is subjected to a polymerization reaction. The aqueous solution may also comprise further monomers, which are co-polymerizable with the α,β-unsaturated carboxylic acid monomers. At least the α,β-unsaturated carboxylic acid has to be partially neutralized, either prior to polymerization of the monomers, during polymerization or post polymerization. In a preferred embodiment of the present invention, the monomers (including α,β-unsaturated carboxylic acid monomers and possible comonomers) are at least 50%, more preferably at least 70%, even more preferably at least 75% and even more preferably from 75% to 95% neutralized.

The monomers in aqueous solution are polymerized by standard free radical techniques, commonly by using a photoinitiator for activation, such as ultraviolet (UV) light. Alternatively, a redox initiator may be used. In this case, however, increased temperatures are necessary.

The water-absorbent resin will preferably be lightly cross-linked to render it water-insoluble. The desired cross-linked structure may be obtained by the co-polymerization of the selected water-soluble monomer and a cross-linking agent possessing at least two polymerizable double bonds in the molecular unit. The cross-linking agent is present in an amount effective to cross-link the water-soluble polymer. The preferred amount of cross-linking agent is determined by the desired degree of absorption capacity and the desired strength to retain the absorbed fluid, that is, the desired absorption under load. Typically, the cross-linking agent is used in amounts ranging from 0.0005 to 5 parts by weight per 100 parts by weight of monomers (including α,β-unsaturated carboxylic acid monomers and possible comonomers) used. If an amount over 5 parts by weight of cross-linking agent per 100 parts is used, the resulting polymer has a too high cross-linking density and exhibits reduced absorption capacity and increased strength to retain the absorbed fluid. If the cross-linking agent is used in an amount less than 0.0005 parts by weight per 100 parts, the polymer has a too low cross-linking density and when contacted with the fluid to be absorbed becomes rather sticky, water-soluble and exhibits a low absorption performance, particularly under load. The cross-linking agent will typically be soluble in the aqueous solution.

Alternatively to co-polymerizing the cross-linking agent with the monomers, it is also possible to cross-link the polymer chains in a separate process step after polymerization.

After polymerization, cross-linking and partial neutralization, the viscous SAPs are dehydrated (i.e. dried) to obtain dry SAPs. The dehydration step can be performed by heating the viscous SAPs to a temperature of about 120° C. for about 1 or 2 hours in a forced-air oven or by heating the viscous SAPs overnight at a temperature of about 60° C. The content of residual water in the dehydrated SAP after drying predominantly depends on dyring time and temperature and can range from 0.5% by weight of dry SAP up to 50% by weight of dry SAP. Preferably, the content of residual water in the dehydrated SAP after drying is 0.5%-45% by weight of dry SAP, more preferably 0.5%-30%, even more preferred 0.5%-15% and most preferred 0.5%-5%.

The SAPs can be transferred into particles of numerous shapes. The term "particles" refers to granules, fibers, flakes, spheres, powders, platelets and other shapes and forms known to persons skilled in the art of SAPs. E.g. the particles can be in the form of granules or beads, having a particle size of about 10 to 1000 μm, preferably about 100 to 1000 μm. In another embodiment, the SAPs can be in the shape of fibers, i.e. elongated, acicular SAP particles. In those embodiments, the SAP fibers have a minor dimension (i.e. diameter of the fiber) of less than about 1 mm, usually less than about 500 μm, and preferably less than 250 μm down to 50 μm. The length of the fibers is preferably about 3 mm to about 100 mm. The fibers can also be in the form of a long filament that can be woven.

According to the present invention the dehydrated SAP particles undergo a surface cross-linking process step. The term "surface" describes the outer-facing boundaries of the particle. For porous SAP particles, exposed internal surfaces may also belong to the surface. The term "surface cross-linked SAP particle" refers to an SAP particle having its molecular chains present in the vicinity of the particle surface cross-linked by a compound referred to as surface cross-linker. The surface cross-linker is applied to the surface of the particle. In a surface cross-linked SAP particle the level of cross-links in the vicinity of the surface of the SAP particle is generally higher than the level of cross-links in the interior of the SAP particle.

Commonly applied surface cross-linkers are thermally activatable surface cross-linkers. The term "thermally activatable surface cross-linkers" refers to surface cross-linkers, which only react upon exposure to increased temperatures, typically around 150° C. Thermally activatable surface cross-linkers known in the prior art are e.g. di- or polyfunctional agents that are capable of building additional cross-links between the polymer chains of the SAPs. Other thermally activatable surface cross-linkers include, e.g., di- or polyhydric alcohols, or derivatives thereof, capable of forming di- or polyhydric alcohols. Representatives of such agents are alkylene carbonates, ketales, and di- or polyglycidylethers. Moreover, (poly)glycidyl ethers, haloepoxy compounds, polyaldehydes, polyoles and polyamines are also well known thermally activatable surface cross-linkers. The cross-linking is based on a reaction between the functional groups comprised by the polymer, for example, an esterification reaction between a carboxyl group (comprised by the polymer) and a hydroxyl group (comprised by the surface cross-linker). As typically a relatively big part of the carboxyl groups of the polymer chain is neutralized prior to the polymerization step, commonly only few carboxyl groups are available for this surface cross-linking process known in the art. E.g. in a 70% percent neutralized polymer only 3 out of 10 carboxylic groups are available for covalent surface cross-linking.

The method of the present invention is applied for surface cross-linking of SAP particles. Hence, the polymer chains comprised by the SAP particles commonly already have been cross-linked by a cross-linker known in the art, comprising at least two polymerizable double bonds in the molecule unit. The cross-linking of different polymer chain segments of the present invention is not intended to bond different SAP particles to each other. Thus, the method of the present invention does not lead to any appreciable inter-particulate bonds between different SAP particles but only results in intra-particulate direct covalent bonds within an SAP particle. If present, such interparticulate direct covalent bonds would hence require additional inter-particulate cross-linking materials.

For the present invention, wherein the polymer chains have already been cross-linked and are thus provided in form of a network, the term "polymer chain segment" refers to the part of the polymer chains between two neighboring, existing cross-links or to the part of the polymer chains between sites, where the polymer chain is branched.

Cross-Linking Molecules

The cross-linking molecules of the present invention comprise at least two C=C double bonds. Preferably, the cross-linking molecules comprise more than two C=C double bonds.

Preferred cross-linking molecules of the present invention are polyfunctional allyl and acryl compounds, such as triallyl cyanurate, triallyl isocyanurate, trimethylpropane tricrylate or other triacrylate esters, pentaerythritol triallyl ether, pentaerythritol tetraallyl ether, butanediol diacrylate, pentaerythritol tetraacrylate, tetra allylorthosilicate, dipentaerythiritol pentaacyralate, di-pentaerythritol hexaacyralate, ethyleneglycol diacrylate, ethyleneglycol dimethacrylate, tetra allyloxy ethane, diallyl phthalate, diethyleneglycol diacrylate, allylmethacrylate, triallylamine, 1,1,1-trimethylolpropane triacrylate, triallyl citrate, or triallyl amine.

Alternatively, the cross-linking molecules are selected from the group consisting of squalene, N,N'methylenebisacrylamide, icosa-pentaenic acid, or sorbic acid.

The most preferred cross-linking molecule of the present invention is triallyl cyanurate.

Radiation Activatable Radical Former Molecules

The radiation activatable radical former molecules are able to form radicals upon electromagnetic radiation.

According to the present invention, the radical former molecules can belong to two different types of radical former: a) Radical former molecules undergoing photo-fragmentation upon irradiation and b) radical former molecules undergoing photo-reduction upon irradiation. The reaction mechanism of both types is described in detail below. According to the present invention, it is not preferred to mix radical former molecules of type a) with radical former molecules of type b).

Radical former molecules of type a) can be selected from the group consisting of dialkyl peroxy-dicarbonates, benzilketales, di-tert-butyl peroxide, di-benzoyl peroxide, bis-(aroyloxyl) peroxides such as bis-(4-methoxy) di-benzoyl peroxide, or bis-(4-methyl) di-benzoyl peroxide, or bis-(4-chlor) di-benzoyl peroxide, 2,4,6-tri-methyl di-benzoyl peroxide, 3-benzoyl benzoic acid, 1,3-dibenzoyl propane, di-benzoyl disulphide, S-phenyl thiobenzoates, acylphosphine oxides, benzoylphosphineoxides, aryl-aryl-sulphides, di-benzyoyl methanes, phenylazo-di-phenyl sulphone, substituted dialkyl peroxy-dicarbonates, substituted benzilketales, substituted di-tert-butyl peroxides, substituted di-benzyoyl peroxides, substituted bis-(aroyloxyl) peroxides such as substituted bis-(4-methoxy) di-benzoyl peroxide, or substituted bis-(4-methyl) di-benzoyl peroxide, or substituted bis-(4-chloro) di-benzoyl peroxide, substituted 2,4,6-tri-methyl di-benzoyl peroxide, substituted 3-benzoyl benzoic acid, substituted 1,3-dibenzoyl propane, substituted O-acyl $\alpha$-oximinoketones, substituted di-benzoyl disulphide, substituted S-phenyl thiobenzoates, substituted acylphosphine oxides, substituted benzoylphosphineoxides, substituted aryl-aryl-sulphides, substituted di-benzoyl methanes, substituted phenylazo-di-phenyl sulphone, the cyclic peroxide of phthalic acid and its derivatives, and the cyclic peroxides of succinic acid and its derivatives. In a preferred embodiment of the invention, such derivatization is done to either enable or further enhance water-solubility.

Radical formers of type b) can be selected from the group consisting of acetophenone, benzophenone, anthraquinone, xanthone, thioxanthone, camphorquinone, terephthalophenone, benzil, fluorenone, $\alpha$-ketocoumarin as well as acetophenone-, benzophenone-, anthraquinone-, xanthone-, thioxanthone-, camphorquinone-, terephthalophenone-, benzil-, fluorenone-, $\alpha$-ketocoumarin-derivatives. Suitable acetophenone derivatives or benzophenone derivatives, for example, also comprise reaction products, such as condensation products of acetophenone derivatives or benzophenone derivatives, comprising at least two acetophenone or benzophenone groups. In a preferred embodiment of the invention, such derivates are chosen to enable or further enhance water-solubility of the radical former molecule.

Alternatively, the radical former molecules of type b) comprise a first group selected from the group consisting of methyl, benzyl, aryl, preferably phenyl and substituted phenyl, and a second group selected from the group consisting of an aryl, an alkyl of 1 to 4 carbon atoms, cyclopropyl, cyclopentyl, cyclohexyl, α,α-dialkoxyalkyl, and α-hydroxyalkyl and wherein the first group is covalently bound to the second group via an additional carbonyl group.

Preferred radical former molecules according to the present invention have a molecular weight of at least Mw=25 g/mol, more preferred at least Mw=60 g/mol, still more preferred at least Mw=120 g/mol, even more preferred at least Mw=180 g/mol and most preferred at least Mw=240 g/mol. Radical former molecules having a relatively high molecular weight often tend to form more stable radicals, as the charge of the radical can be distributed better within the radical. Without wishing to be bound be theory, it is believed that if the radical were very unstable, it more likely reacts to recombine to the radical former molecule.

Furthermore, preferred radical former molecules according to the present invention will comprise aromatic groups, such as arenes. This also leads to more stable radicals as the unpaired electron can be distributed throughout the aromatic group.

Particularly preferred radical former molecules of the present invention are acetophenone- or benzophenone-derivatives.

Suitable acetophenone derivatives or benzophenone derivatives are described, for example, in European Patent Application EP-A-0 346 734; European Patent Application EP-A-0 377 199; European Patent Application EP-A-0 246 848; German Patent Application DE-A-4 037 079 and German Patent Application DE-A-3 844 444.

Reaction Mechanism:

In the following, the principal reaction mechanism according to the present invention is depicted.

a) Radical Former Molecules Undergoing Photo-Fragmentation Upon Irradiation

The radical former molecule of this type comprises a labile bond, and is hereinafter generally depicted as $R_a$—$R_b$. Upon electromagnetic irradiation, preferably UV radiation, the labile bond breaks, whereby two radicals ($R_a$· and $R_b$·) are formed according to Formula 1. This homolytic cleavage may result in two identical radicals, if the labile bond comprised by the radical former molecule (so-called precursor molecule) divides the molecule into two identical parts. Alternatively, the homolytic cleavage may result in two different radicals.

Formula I:

The radicals, which have been formed, can now react with an aliphatic C—H group comprised by a polymer chain segment of the SAP particle forming a carbon-centered radical at this polymer chain segment according to Formula 2. Alternatively, the radicals formed from the radical former molecule, can react with one of the C=C double bonds comprised by the cross-linking molecule to form a radical consisting of the reaction product of the cross-linking molecule and the initial radical according to Formula 3.

Formula 2:

Formula 3:

The carbon-centered radical within the polymer chain segment formed in the reaction of Formula 2 can react with the radical formed in Formula 3. The reaction product of this reaction is a polymer chain segment, which has the reaction products of the radical former molecule and the cross-linking molecule bound thereto according to Formula 4.

Formula 4:

Thereafter, the radicals formed from the radical former molecule in Formula 1, can react with the second of the C=C double bonds of the cross-linking molecule, which is comprised in the reaction product of Formula 4. This reaction is depicted in Formula 5:

Formula 5:

To form the cross-link between two polymer chain segments, the carbon-centered radical which is comprised in the reaction product of Formula 5 combines with another carbon centered radical located at a polymer chain segment, which forms as described by Formula 2, closing the cross-link. This reaction is depicted in Formula 6.

Formula 6:

Hence, the net reaction when using radical former molecules undergoing photo-fragmentation upon irradiation is the formation of a cross-link between two polymer chain segments, wherein the cross-link comprises the reaction product of one cross-linking molecule with two C=C double bonds and two radical former molecules. The net reaction is depicted in Formula 7:

Formula 7:

In case of symmetric radical former molecules which form two identical radicals, it is possible, to recycle the resulting $R_a$—H and/or $R_b$—H molecules in order to regain the initial radical former molecules.

In the above described reaction mechanism, side reactions may theoretically take place, such as:

Recombination of two radicals formed upon homolytic cleavage of the radical former molecule. However, the recombined radical former molecule may again form radicals upon electromagnetic irradiation, or

Two carbon-centered radicals formed at different polymer chain segments according to Formula 2 may combine to form a direct covalent bond between these polymer chain segments. As this side reaction also leads to the formation of a cross-link between two polymer chain segments, this side reaction does not have any negative impact on the present invention.

b) Radical Former Molecules Undergoing Photo-Reduction upon Irradiation

Radical former molecules undergoing photo-reduction upon irradiation comprise carbonyl groups. In preferred embodiments of the present invention, such radical former molecules are ketones.

Upon electromagnetic irradiation, preferably upon irradiation by UV light, the radical former molecules of this type are transferred in an "excited state" (triplet state) according to Formula 8. Hence, they are not yet transformed into a radical, but are much more reactive than before they were irradiated.

Formula 8:

In the next step, the radical former molecule in its excited state reacts with an aliphatic C—H group comprised by a polymer chain segment and abstracts a hydrogen radical, thereby forming a carbon-centered radical at this polymer chain segment and a ketyl radical according to Formula 9:

Formula 9:

The ketyl radical can now react with one of the C=C double bonds of the cross-linking molecule, whereby the ketyl radical reacts with the cross-linking molecule (addition reaction to the C=C double bond), thus forming another radical according to Formula 10:

Formula 10:

The carbon-centered radical within the polymer chain segment formed in the reaction of Formula 8 can now react with the radical formed in Formula 10. The reaction product of this reaction is a polymer chain segment, which has the reaction products of the radical former molecule and the cross-linking molecule bound thereto according to Formula 11.

Formula 11:

Thereafter, the ketyl radical formed from the radical former molecule in Formula 9, can react with the second of the C=C double bonds of the cross-linking molecule, which is comprised in the reaction product of Formula 11. This reaction is depicted in Formula 12:

Formula 12:

To form the cross-link between two polymer chain segments, the carbon-centered radical which is comprised in the reaction product of Formula 12 combines with another carbon centered radical located at a polymer chain segment, which forms as described by Formula 9, closing the cross-link. This reaction is depicted in Formula 13.

Formula 13:

Hence, the net reaction when using radical former molecules undergoing photo-reduction upon irradiation is the formation of a cross-link between two polymer chain segments, wherein the cross-link comprises the reaction product of one cross-linking molecule with two C=C double bonds and two radical former molecules. The net reaction is depicted in Formula 14:

Formula 14:

In the above described reaction mechanism, side reactions may theoretically take place, such as:
  Combination of two ketyl radicals formed upon homolytic cleavage of the radical former molecule, or
  Two carbon-centered radicals formed at different polymer chain segments according to Formula 2 may combine to form a direct covalent bond between these polymer chain segments. As this side reaction also leads to the formation of a cross-link between two polymer chain segments, this side reaction does not have any negative impact on the present invention.

According to the present invention, radical former molecules undergoing photo-reduction upon irradiation are preferred over radical former molecules undergoing photo-fragmentation.

It should be noted, that in the case of radical former molecules undergoing photo-fragmentation are applied, only a part of the radical former molecule is comprised by the cross-link between the polymer chain segments, whereas for radical former molecules undergoing photo-reduction, the complete radical former molecule in its reduced form (with a carbonyl group being reduced to a hydroxyl group) is comprised by the cross-link between the polymer chain segments.

Hence, for radical former molecules undergoing photo-fragmentation, the reaction product comprised by the cross-link between polymer chain segments is only a part of the initial radical former molecule—typically one half of the initial molecule.

For radical former molecules undergoing photo-reduction, the reaction product comprised by the cross-link between polymer chain segments is the complete radical former molecule in its reduced form (with a carbonyl group being reduced to a hydroxyl group).

The reaction product of the cross-linking molecule—for both types of radical former molecules—is the initial cross-linking molecule, wherein those C=C double bonds, which have reacted with the radicals formed from the radical former molecules (or have reacted directly with the carbon-centered radicals formed in the polymer chain segments) are converted into C—C single bonds.

As the reaction substantially only takes place at the surface of the SAP particles, the cross-links between polymer chain segments according to the present invention are mainly present on the surface of the SAP particles, although a few of those cross-links may also be formed inside the SAP particles. This is because a small amount of the surface cross-linking composition may penetrate inside the SAP particles after the composition has been applied onto the SAP particle surfaces. However, these cross-links between polymer chain segments inside the SAP particles are not an objective of the present invention but only may take place unavoidably to a very small degree.

In preferred embodiments of the present invention—for both types of radical former molecules—the cross-linking molecules comprise more than two C=C double bonds. In these embodiments, more than two polymer chain segments can be cross-linked to each other, following the reaction mechanism described above. In these embodiments, the number of reaction products of radical former molecules comprised by the cross-link equals the number of C=C double bonds comprised by the cross-linking molecule.

It is believed, that in embodiments, wherein more than two polymer chain segments are cross-linked to each other, the efficiency of the reaction as well as the stability of the resulting product is significantly enhanced.

Without wanting to be bound by theory, it is believed that the rate determining step of a radically initiated cross-linking reaction in the absence the cross-linking molecule is the so-called recombination of two carbon centered radicals, forming a direct covalent bond between two polymer chain segments. This recombination follows a kinetic law of a second order reaction, i.e. the reaction rate of such combination reaction is proportional to the product of the concentrations of the two combining carbon centered radical species. To form a new covalent bond, the two carbon centered radicals need to hit each other during their short lifetime, despite their distance and possible sterical obstructions due to the rigidity of the polymer chains to be connected.

If, however, a cross-linking molecule is added according to the present invention, it is believed, that the reaction between the cross-linking molecule or its reaction product—i.e. the radical formed according to Formula 3 for type a) radical formers, respectively, the radical formed according to Formula 11 for type b) radical formers—and the carbon centered radical in the polymer chain, forming a covalent bond, follows a kinetic law of pseudo-first order, i.e. the reaction rate is believed to be only proportional to the concentration of the carbon centered radical, since the concentration of the second reaction partner, i.e. the cross-linking molecule respectively its reaction product, is so high that it can be regarded as constant throughout the reaction. Reactions of pseudo-first order kinetics are known to be kinetically favored versus reactions of second order kinetics, i.e. they have a higher reaction speed, in particular if the reactive species, in this case the intermediate carbon centered radical in the polymer chain, are low in concentration. As a result thereof, the overall process can be run at a higher line speed due to the presence of the surface cross-linker and its kinetically favorable influence on the rate-determining step of the overall reaction.

As another consequence thereof, the overall process is more robust towards the presence of oxygen due to the presence of the surface-cross-linker. Oxygen is known as a radical-scavenger that readily reacts with carbon-centered radicals. If the desired reaction of the carbon-centered radicals is accelerated, as it is believed in the case of the present invention, without wanting to be bound by theory, the unwanted side reaction with oxygen can be at least partly circumvented. Hence, the necessary process measures to suppress presence of oxygen during the reaction do not need to be exerted as rigorously, which may facilitate processing and decrease capital cost.

The SAP particles of the present invention can be analyzed by 13C-NMR or 1H-NMR methods well known in the art to detect the reaction product of the cross-linking molecules having at least two C=C double bonds and of the radical former molecules.

Process:

Above-mentioned radiation-activateable surface cross-linking compositions are capable of forming covalent bonds by exposure to electromagnetic radiation. Electron beams as well as UV-light can produce suitable electromagnetic radiation. Preferably, according to the present invention UV-light is used with a wave-length of 220-380 nm, selected on the selected radical former molecule(s). The UV-light may be used in combination with an electron-beam, and also in combination with an IR-light. In case of combination of UV-irradiation with other electromagnetic radiation, it is not critical if the application of the UV-light takes place simultaneously with the other electromagnetic irradiation (i.e. electron-beam or IR-light), or if irradiation is done in a series of different irradiation steps. For radical former molecules, which require a relative high amount of activation energy, activation with electron beams may be necessary.

In the present invention the surface cross-linking composition is applied in amounts of less than 25% by weight of SAP particle, preferably in amounts of less than 15%, more preferably in amounts of less than 5%, even more preferably in amounts from 0.1% to 5% and most preferably in amounts from 0.1% to 1.5%.

The ratio of the cross-linking molecule to the radical former molecule is preferably in the range of 0.2 to 5, even more preferred between 0.33 and 3 and mostly preferred in the range of 1 to 3, with said ratios being molar ratios.

The surface cross-linking composition may be sprayed onto the SAP particles by means of a fluidized-bed spraying chamber. Simultaneously IR-irradiation may be applied to accomplish drying and simultaneously UV-light may be applied to accomplish cross-linking in the fluidized-bed.

However, in certain cases drying and cross-linking may take place in two steps in series, which could be carried out in any order. Instead or in combination with IR-light, any conventional drying equipment can be used in the drying step. However, in certain embodiments of the present invention little or no drying is required, e.g. in cases, where only a small amount of the surface cross-linking composition is applied dissolved in small amounts of solution.

In particular, the radiation activatable radical former molecules may upon activation by irradiation react with aliphatic C—H bond comprised by a nearby polymer chain segment, abstracting a hydrogen radical and leaving a carbon centered radical. Theoretically, the radiation activatable radical former molecules may upon radiation also react with carboxyl groups comprised by the polymer chain segments. However, it is much more likely that the radical formed from the radical former molecule will react with the aliphatic C—H bond, as it is rather unlikely that the radical will be able to abstract a hydrogen radical from the carboxyl group, which is strongly polarized.

Hence, compared to prior art surface cross-linking, the cross-linking process of the present invention is not restricted to the carboxyl groups but also comprises the numerous aliphatic groups within the polymer chains of the SAP. Hence, according to the present invention the number of available reaction sites for the surface cross-linking process of the SAP particles is strongly increased. Therefore, it is possible to achieve a far more homogenous, uniform surface cross-linking compared to the surface cross-linking known from the art. Furthermore, it is possible to surface cross-link the SAP to a higher degree than the SAP known from the prior art. This enables to make the SAP particles much stiffer, thus, to more effectively inhibit the gel-blocking effect at a given degree of neutralization. Moreover, it is possible to increase the capacity of the SAP particles.

As the surface cross-linking composition is applied on the surface of the SAP particles, the reaction takes mainly place on the surface of the SAP particles. That means, that mainly aliphatic groups, which are exposed in the vicinity of the surface of the SAP particles, undergo a cross-linking process, leading to SAP particles with a high degree of cross-linking on their surface while not substantially affecting the inner core (=interior portion) of the SAP particles. Hence, the percentage of the reaction product of the radiation activatable radical former molecules and the cross-linking molecules on the surface of the SAP particles will preferably be higher than the percentage of said reaction product inside the SAP particles.

The UV irradiation for the surface cross-linking can preferably be carried out in a conventional manner with UV lamps having a power between 50 W and 2 kW, more preferably between 200 W and 700 W, and even more preferred between 400 W and 600 W. Irradiation time is preferably between 0.1 sec. and 30 min., more preferably between 0.1 sec. and 15 min, even more preferably between 0.1 sec. and 5 min and most preferably between 0.1 sec. and 2 min. Commercially available mercury pressure UV-lamps can be used. The choice of the lamp depends on the absorption spectrum of the radical former molecules used. Lamps having a higher power generally permit more rapid cross-linking.

The distance between the UV-lamp(s) and the SAP which is to be cross-linked preferably varies between 5 cm and 15 cm.

Compared to the surface cross-linking known from the prior art, the surface cross-linking according to the present invention is much quicker. Prior art surface cross-linking reactions carried out under increased temperatures commonly take up to 45 minutes. This time consuming process step renders the manufacturing process of SAP particles less economic than desirable. On the contrary, the cross-linking process according to the present invention can be carried out very quickly and hence, strongly adds to a much more efficient and economic overall manufacturing process.

Furthermore, as the surface cross-linking reaction proceeds quickly, the molecules comprised by the surface cross-linking composition applied on the surface of the SAP particles have less time to penetrate inside the SAP particles. As a result, the surface cross-linking process is mainly restricted to the surface of the SAP particles and avoids undesired further cross-linking reactions inside the SAP particles.

Another advantage of the present invention refers to the neutralization step. The $\alpha,\beta$-unsaturated carboxylic acid monomers are often neutralized prior to the polymerization step (pre-neutralization). Compounds, which are useful to neutralize the acid groups of the monomers, are typically those, which will sufficiently neutralize the acid groups without having a detrimental effect on the polymerization process. Such compounds include alkali metal hydroxides, alkali metal carbonates and bicarbonates. Preferably, the material used for neutralization of the monomers is sodium or potassium hydroxide or carbonate. The neutralizing compound is preferably added to an aqueous solution comprising the $\alpha,\beta$-unsaturated carboxylic acid monomers (pre-neutralization). As a result, the carboxyl groups comprised by the $\alpha,\beta$-unsaturated carboxylic acid monomers are at least partially neutralized. Consequently,—after the polymerization step—also the carboxyl groups comprised by the $\alpha,\beta$-unsaturated carboxylic acid of the polymer are at least partially neutralized. In case sodium hydroxide is used, neutralization results in sodium acrylate, which dissociates in water into negatively charged acylate monomers and positively charged sodium ions.

If the final SAP particles are in the swollen state, after they absorbed aqueous solution, the sodium ions are freely movable within the SAP particles. In absorbent articles, such as diapers or training pants, the SAP particles typically absorb urine. Compared to distilled water, urine comprises a relatively high amount of salt, which at least partly is present in dissociated form. The dissociated salts comprised by the urine make absorption of liquid into the SAP particles more difficult, as the liquid has to be absorbed against an osmotic pressure caused by the ions of the dissociated salts. The freely movable sodium ions within the SAP particles strongly facilitate the absorption of liquid into the particles, because they reduce the osmotic pressure. Therefore, a high degree of neutralization can largely increase the capacity of the SAP particles and the speed of liquid absorption.

The surface cross-linkers known in the art react with the carboxyl groups of the polymer. Hence, the degree of neutralization has to be balanced with the need to surface cross-link, because both process steps make use of the carboxyl groups.

According to the present invention, the surface cross-linking composition comprises radiation activatable radical former-molecules, which—once activated e.g. by UV radiation—are able to react with the aliphatic groups comprised by the polymer. Therefore, it is possible to neutralize the monomers to a larger degree without significantly diminishing the possibility of later surface cross-linking.

According to the present invention, the carboxyl groups comprised by the $\alpha,\beta$-unsaturated carboxylic acid monomers are preferably at least 50%, more preferably at least 70%, even more preferably at least 75% and even more preferably between 75% and 95% neutralized. Hence, also the carboxyl groups comprised by the $\alpha,\beta$-unsaturated carboxylic acid of the polymer are at least 50%, more preferably at least 70%, even more preferably at least 75% and even more preferably between 75% and 95% neutralized.

A still further advantage of the present invention is the reduction of undesired side-reactions during the surface cross-linking process. Surface cross-linking known from the prior art requires increased temperatures, commonly around or above 150°. At these temperatures, not only the surface cross-linking reaction is achieved, but also a number of other reactions take place, e.g. anhydride-formation within the polymer or dimer cleavage of dimers previously formed by the acrylic acid monomers. These side-reactions are highly undesired, because they result in SAP particles with decreases capacity.

As the surface cross-linking process according to the present invention does not necessarily need increased temperatures but can also be carried out at moderate temperatures using electromagnetic radiation, such as UV radiation, those side-reactions are considerably reduced. According to the present invention, the surface cross-linking reaction can preferably be accomplished at temperatures of less than 100° C., preferably at temperatures less than 80° C., more preferably at temperatures less than 50° C., even more preferably at temperatures less than 40° C., most preferably at temperatures between 20° C. and 40° C. In an additional process step drying of the SAP is typically carried out at temperatures above 100° C.

At elevated temperatures around or above 150° C. commonly applied in the surface cross-linking process known from the prior art, the SAP particles sometimes change their color from white to yellowish. As according to the surface cross-linking process of the present invention, it is possible to carry out the surface cross-linking process under moderate temperatures, the problem of color degradation of the SAP particles is strongly reduced.

According to the present invention, the surface cross-linking composition may comprise only one type of cross-linking molecules, or may, alternatively, comprise two or more chemically different cross-linking molecules. Likewise, the surface cross-linking composition may comprise only one type of radiation activatable radical former molecule, or may, alternatively, comprise two or more chemically different radiation activatable radical former molecules.

As a further alternative, surface cross-linking composition of the present invention can be applied together with one or more thermally activatable surface cross-linkers, e.g. 1,4-butandiol. In this embodiment, the SAP particles further have to comprise carboxyl groups wherein at least some of the carboxyl groups are at least partially exposed on the outer surface of the SAP particles and wherein the thermally activated surface cross-linker is covalently bound to at least a part of the carboxyl groups at least partially exposed on the surface of said SAP particles.

In case the surface cross-linking composition of the present invention is used together with a thermally activatable surface cross-linker, both UV radiation and increased temperatures (above 140° C.) are necessary for the surface cross-linking process.

In these embodiments, the surface of the resulting SAP particles will further comprise the reaction product of the thermally activatable surface cross-linker.

The surface cross-linking composition is preferably used in a liquid solution, more preferably in an aqueous solution.

To obtain SAP particles with evenly distributed surface cross-linking, the surface cross-linking composition has to be distributed evenly on the SAP particle prior to or during UV radiation. Therefore, the surface cross-linker is preferably applied by spraying onto the SAP particles.

The method of the present invention may further comprise an optional washing step to wash off unreacted molecules comprised by the surface cross-linking composition or to wash off molecules formed by side reactions.

Absorbent Articles

The SAP particles of the present invention are preferably applied in absorbent articles. As used herein, absorbent article refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, diaper holders and liners, sanitary napkins and the like.

Preferred absorbent articles of the present invention are diapers. As used herein, "diaper" refers to an absorbent article generally worn by infants and incontinent persons about the lower torso.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

Figure 1:
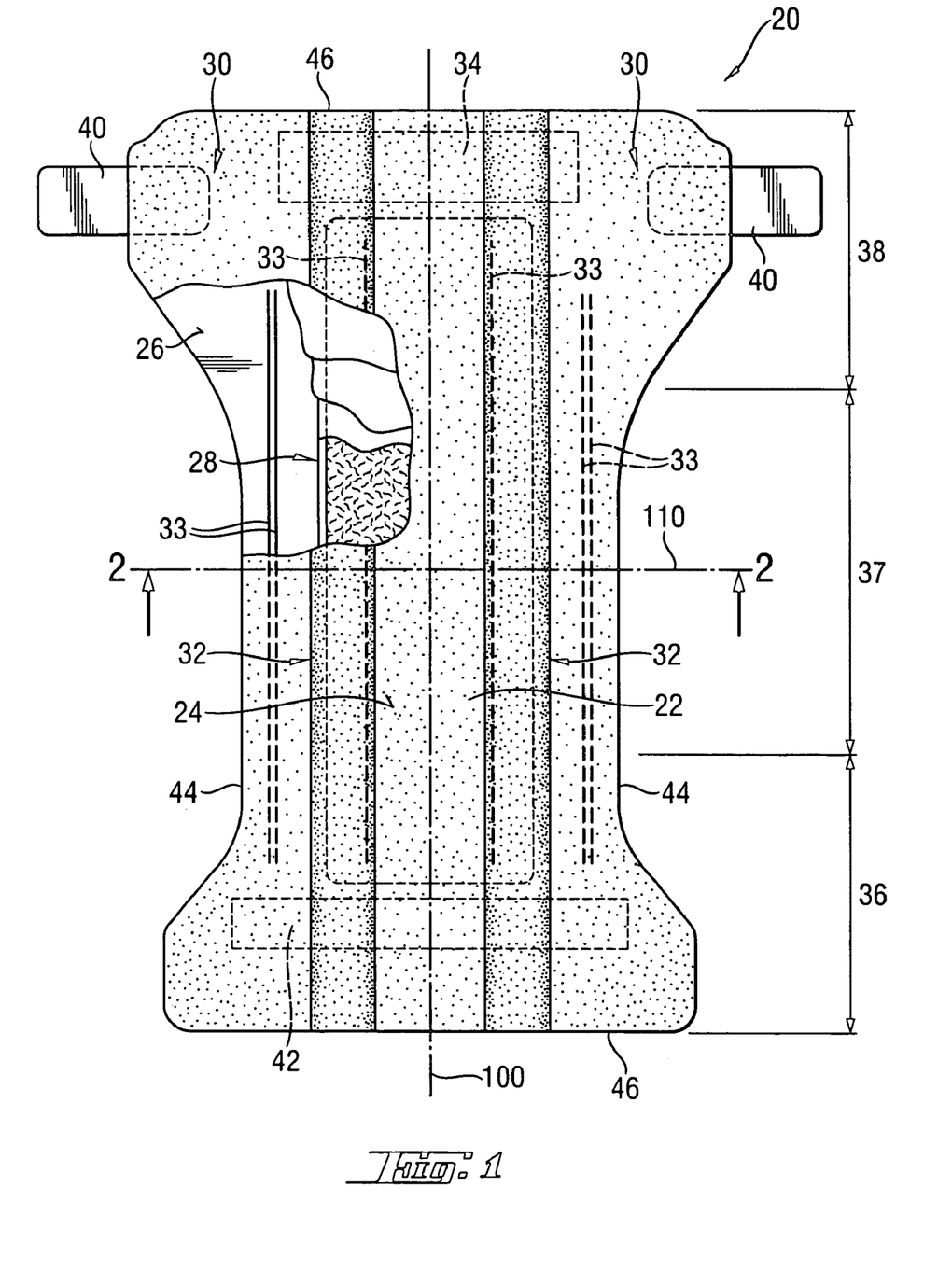
FIG. 1 is a top plan view of a disposable diaper, with the upper layers partially cut away.

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis 22 may also include most or all of the absorbent core 28 encased between the topsheet 24 and the backsheet 26. The chassis 22 preferably further includes side panels 30, leg cuffs 32 with elastic members 33 and a waist feature 34. The leg cuffs 32 and the waist feature 34 typically comprise elastic members. One end portion of the diaper is configured as the front waist region 36 of the diaper 20. The opposite end portion is configured as the rear waist region 38 of the diaper 20. The intermediate portion of the diaper is configured as the crotch region 37, which extends longitudinally between the front and rear waist regions. The crotch region 37 is that portion of the diaper 20 which, when the diaper is worn, is generally positioned between the wearer's legs.

The waist regions 36 and 38 may include a fastening system comprising fastening members 40 preferably attached to the rear waist region 38 and a landing zone 42 attached to the front waist region 36.

The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

The diaper may also include other features as are known in the art including front and rear ear panels, waist cap features, elastics and the like to provide better fit, containment and aesthetic characteristics.

The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminute wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, absorbent gelling materials, or any other known absorbent material or combinations of materials. The absorbent core may further comprise minor amounts (typically less than 10%) of non-liquid absorbent materials, such as adhesives, waxes, oils and the like.

Furthermore, the SAP particles of the present invention can be applied as absorbent materials. The SAP particles of the present invention preferably are present in amounts of at least 50% by weight of the whole absorbent core, more preferably at lest 60%, even more preferably at least 75% and still even more preferably at least 90% by weight of the whole absorbent core.

Figure 2:
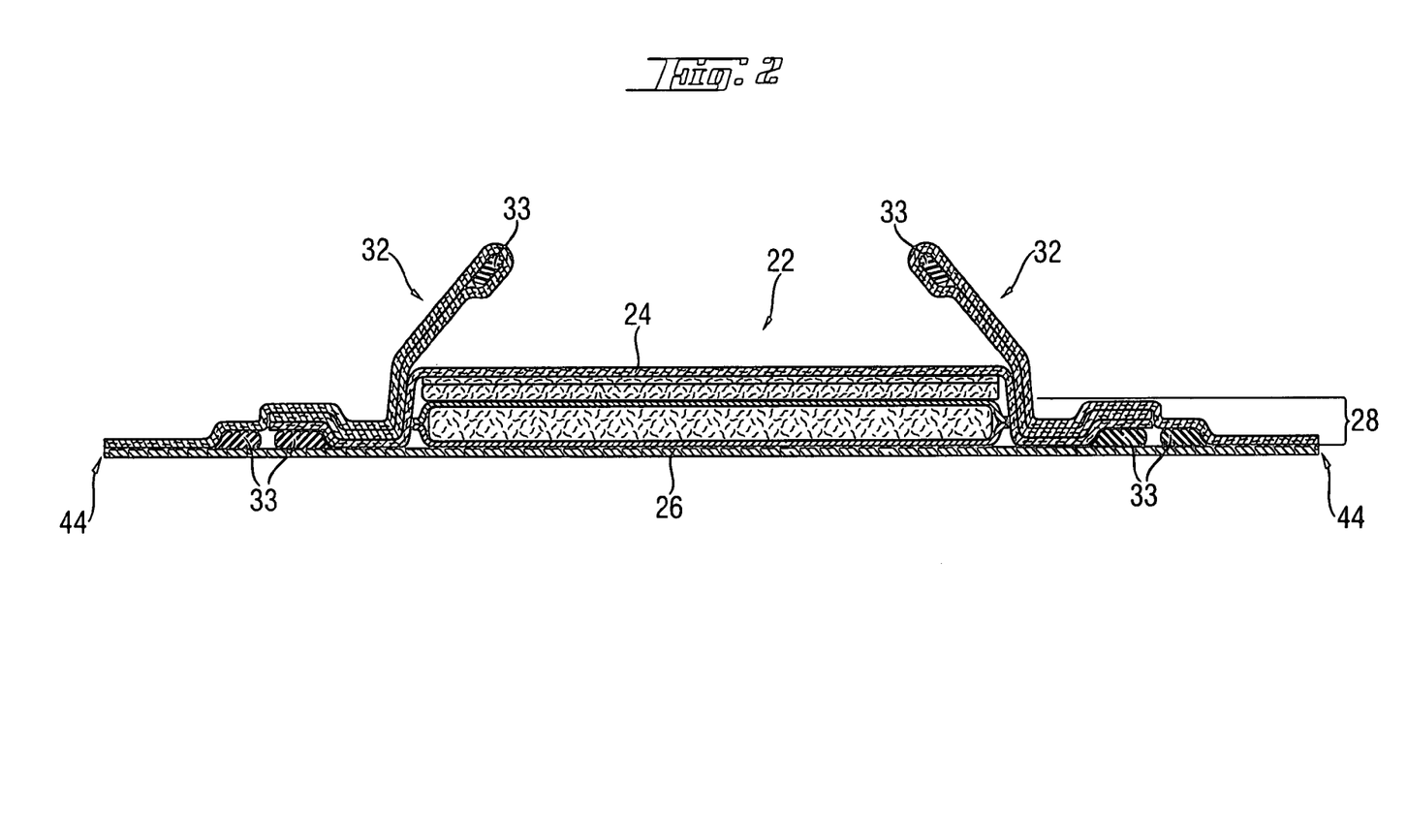
FIG. 2 is a cross-sectional view of the disposable diaper shown in FIG. 1

FIG. 2 shows a cross-sectional view of FIG. 1 taken in the transverse axis 110. In FIG. 2 illustrates a preferred embodiment of the different zones comprised by the absorbent cores. In FIG. 2, the fluid acquisition zone 50 comprises an upper acquisition layer 52 and a lower acquisition layer 54, while the fluid storage zone underneath the fluid acquisition zone comprises a storage layer 60, which is wrapped by an upper core wrap layer 56 and a lower core wrap layer 58.

In one preferred embodiment the upper acquisition layer comprises a nonwoven fabric whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably is in direct contact with the storage layer.

In a preferred embodiment the core wrap material comprises a top layer and a bottom layer, which layers may be sealed together along their edges, e.g. by adhesive. The top layer and the bottom layer can be provided from a non-woven material. The top layer and the bottom layer may be provided from two or more separate sheets of materials or they may be alternatively provided from a unitary sheet of material. Such a unitary sheet of material may be wrapped around the storage layer, e.g. in a C-fold.

The storage layer the present invention typically comprises SAP particles mixed with fibrous materials. Other materials as suitable for the absorbent core may also be comprised.

All documents cited in the Detailed Description of the Invention, are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A superabsorbent polymer, comprising:
   a. particles selected from the group consisting of granules, flakes, spheres, powders, platelets, and beads, each of the particles comprising a surface and a core, wherein a plurality of aliphatic C—H groups are present at the surface; and
   b. polymer chain segments, wherein at least some of said polymer chain segments are covalently surface cross-linked to each other after formation of said superabsorbent polymer particles, wherein at least some of the surface cross-links comprise the reaction product of cross-linking molecules having at least two C=C double bonds, and wherein at least some of the surface cross-links comprise the reaction product of radical former molecules that chemically react with the aliphatic C—H groups when the radical former molecules are activated.

2. The superabsorbent polymer according to claim 1, wherein said radical former molecules are radical former molecules that undergo photoreduction upon irradiation.

3. The superabsorbent polymer according to claim 1, wherein at least some of said surface cross-links comprise the reaction products of at least two chemically different cross-linking molecules.

4. The superabsorbent polymer according to claim 1, wherein at least some of said surface cross-links comprise the reaction products and of at least two chemically different radical former molecules.

5. A method of surface cross-linking superabsorbent polymer particles which comprises the steps of
   a) providing discrete superabsorbent polymer particles selected from the group consisting of granules, flakes, spheres, powders, platelets, and beads, each of the particles comprising a surface and a core, wherein a plurality of aliphatic C—H groups are present at the surface, the particles comprising polymer chain segments;
   b) adding a surface cross-linking composition comprising cross-linking molecules having at least two C=C double bonds and further comprising radical former molecules wherein the radical former molecules when activated are configured to chemically react with the aliphatic C—H groups; and
   c) exposing said superabsorbent polymer particles and said surface cross-linking composition to electromagnetic irradiation capable of activating said radical former,
   whereby said cross-linking molecules and said radical former molecules react with at least some of said polymer chain segments comprised at surfaces of the superabsorbent polymer particles to form covalent cross-links between said polymer chain segments, wherein said cross-links comprise the reaction product of said cross-linking molecule, wherein said cross-links further comprise the reaction product of said radical former molecules, and wherein the method does not lead to any appreciable interparticulate bonds between the superabsorbent polymer particles.

6. The method according to claim 5, wherein said electromagnetic irradiation is ultraviolet radiation.

7. The method according to claim 5, wherein said radical former molecules are radical former molecules that undergo photoreduction upon irradiation.

8. The method according to claim 5, wherein said cross-linking composition comprises at least two chemically different cross-linking molecules.

9. The method according to claim 5, wherein said cross-linking composition comprises at least two chemically different radical former molecules.

10. The method according to claim 5, wherein said method is carried out at temperatures of less than 100° C.

11. The method according to claim 5, wherein said surface cross-linking composition further comprises a solvent and wherein said method further comprises the step of drying said superabsorbent polymer particles, said drying being carried out after step c) of claim 5.

12. An absorbent article comprising a substantially liquid pervious topsheet, a substantially liquid impervious backsheet and an absorbent core between said topsheet and said backsheet, wherein said absorbent article comprises the superabsorbent polymer according to claim 1.

13. An absorbent article comprising superabsorbent polymer particles, said superabsorbent polymer particles being surface cross-linked according to the method of claim 5.

* * * * *

UNITED STATES PATENT AND TRADEMARK OFFICE
CERTIFICATE OF CORRECTION

PATENT NO. : 7,588,777 B2  Page 1 of 1
APPLICATION NO. : 11/183356
DATED : September 15, 2009
INVENTOR(S) : Flohr et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 892 days.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

PATENT NO.        : 7,588,777 B2
APPLICATION NO.   : 11/183356
DATED             : September 15, 2009
INVENTOR(S)       : Andreas Flohr et al.

It is certified that error appears in the above-identified patent and that said Letters Patent is hereby corrected as shown below:

Column 8
Line 33, delete "di-benzyoyl" and insert --di-benzoyl--.
Lines 35 and 36, delete "di-benzyoyl" and insert --di-benzoyl--.

Signed and Sealed this
Twenty-fifth Day of January, 2011

David J. Kappos
*Director of the United States Patent and Trademark Office*